US009440058B2

(12) United States Patent
Osborne et al.

(10) Patent No.: US 9,440,058 B2
(45) Date of Patent: Sep. 13, 2016

(54) DEVICE FOR ENABLING REPEATED ACCESS TO A VESSEL

(75) Inventors: Thomas A. Osborne, Bloomington, IN (US); Michael H. Palne, Jylinge (DK)

(73) Assignee: Cook Medical Technologies, LLC, Bloomington, IN (US)

(*) Notice: Subject to any disclaimer, the term of this patent is extended or adjusted under 35 U.S.C. 154(b) by 1082 days.

(21) Appl. No.: 12/316,734

(22) Filed: Dec. 16, 2008

(65) Prior Publication Data

US 2009/0157014 A1 Jun. 18, 2009

Related U.S. Application Data

(60) Provisional application No. 61/007,948, filed on Dec. 17, 2007.

(51) Int. Cl.
*A61F 2/07* (2013.01)
*A61M 39/02* (2006.01)
*A61M 39/04* (2006.01)
*A61M 1/36* (2006.01)

(52) U.S. Cl.
CPC ....... *A61M 39/0208* (2013.01); *A61M 1/3661* (2014.02); *A61M 39/04* (2013.01); *A61M 2039/0238* (2013.01)

(58) Field of Classification Search
CPC ........................................................ A61F 2/07
USPC .................... 623/1.35–1.36; 604/9, 256
See application file for complete search history.

(56) References Cited

U.S. PATENT DOCUMENTS

| 5,741,325 | A | | 4/1998 | Chaikof et al. |
| 5,833,654 | A | * | 11/1998 | Powers et al. ............. 604/93.01 |
| 5,984,955 | A | * | 11/1999 | Wisselink ..................... 623/1.35 |
| 6,004,301 | A | * | 12/1999 | Carter ........................... 604/256 |
| 6,042,569 | A | * | 3/2000 | Finch et al. ................... 604/175 |
| 6,159,182 | A | * | 12/2000 | Davis et al. ............. 604/167.06 |
| 6,361,555 | B1 | | 3/2002 | Wilson |
| 6,459,917 | B1 | * | 10/2002 | Gowda et al. ................ 600/345 |
| 6,468,301 | B1 | | 10/2002 | Amplatz et al. |
| 6,582,394 | B1 | | 6/2003 | Reiss et al. |
| 6,585,760 | B1 | | 7/2003 | Fogarty |
| 6,626,939 | B1 | | 9/2003 | Burnside et al. |
| 6,793,672 | B2 | | 9/2004 | Khosravi et al. |
| 6,908,477 | B2 | * | 6/2005 | McGuckin et al. ......... 623/1.11 |
| 6,932,827 | B2 | * | 8/2005 | Cole ............................. 606/153 |
| 6,932,837 | B2 | | 8/2005 | Amplatz et al. |
| 6,974,473 | B2 | | 12/2005 | Barclay et al. |
| 7,059,330 | B1 | * | 6/2006 | Makower et al. ............ 128/898 |
| 7,108,716 | B2 | | 9/2006 | Burnside et al. |
| 7,232,449 | B2 | * | 6/2007 | Sharkawy et al. ............ 606/153 |
| 7,261,705 | B2 | * | 8/2007 | Edoga et al. ............ 604/288.02 |

(Continued)

FOREIGN PATENT DOCUMENTS

| EP | 0923912 B1 | 2/2004 |
| EP | 1185215 B1 | 4/2007 |

(Continued)

*Primary Examiner* — Suzette J Gherbi
(74) *Attorney, Agent, or Firm* — Brinks Gilson & Lione; John C. Bacoch

(57) ABSTRACT

An implantable prosthesis with at least one fenestration in a side wall of that prosthesis is disclosed. The fenestration provides an access port through which a medical device (such as a needle or a cannula) can be directed to enable access to the lumen of the blood vessel which the prosthesis is supporting.

22 Claims, 7 Drawing Sheets

(56) References Cited

U.S. PATENT DOCUMENTS

| | | | |
|---|---|---|---|
| 7,296,782 B2 * | 11/2007 | Enerson et al. | 251/149.7 |
| 7,799,064 B2 * | 9/2010 | Brucker et al. | 623/1.11 |
| 7,993,365 B2 * | 8/2011 | Morris et al. | 606/213 |
| 2002/0035392 A1 | 3/2002 | Wilson | |
| 2003/0023299 A1 | 1/2003 | Amplatz et al. | |
| 2003/0195606 A1 * | 10/2003 | Davidson et al. | 623/1.11 |
| 2004/0073238 A1 * | 4/2004 | Makower | 606/153 |
| 2004/0102795 A1 * | 5/2004 | Yencho et al. | 606/153 |
| 2004/0215327 A1 | 10/2004 | Doig et al. | |
| 2005/0080401 A1 * | 4/2005 | Peavey | 604/891.1 |
| 2005/0283224 A1 | 12/2005 | King | |
| 2005/0288767 A1 * | 12/2005 | Kujawski et al. | 623/1.13 |
| 2006/0064159 A1 * | 3/2006 | Porter et al. | 623/1.24 |
| 2006/0247605 A1 * | 11/2006 | Edoga et al. | 604/891.1 |
| 2006/0282149 A1 * | 12/2006 | Kao | 623/1.11 |
| 2007/0167901 A1 * | 7/2007 | Herrig et al. | 604/6.16 |
| 2007/0265584 A1 * | 11/2007 | Hickman et al. | 604/288.01 |
| 2008/0108930 A1 * | 5/2008 | Weitzel et al. | 604/5.04 |
| 2008/0275542 A1 * | 11/2008 | LaDuca et al. | 623/1.35 |
| 2008/0306580 A1 * | 12/2008 | Jenson et al. | 623/1.11 |
| 2009/0012596 A1 * | 1/2009 | Kocur et al. | 623/1.11 |
| 2009/0276031 A1 * | 11/2009 | Kao | 623/1.11 |
| 2010/0222869 A1 * | 9/2010 | Delaney | 623/1.26 |
| 2010/0286705 A1 * | 11/2010 | Vassiliades, Jr. | 606/108 |
| 2011/0295364 A1 * | 12/2011 | Konstantino et al. | 623/1.35 |

FOREIGN PATENT DOCUMENTS

| | | |
|---|---|---|
| EP | 1400218 B1 | 2/2008 |
| EP | 1673040 B1 | 7/2008 |
| EP | 1267750 B1 | 10/2008 |
| WO | WO9509586 A1 | 4/1995 |
| WO | WO0071054 | 11/2000 |
| WO | WO0145594 A2 | 6/2001 |
| WO | WO03055414 | 7/2003 |
| WO | WO2005034809 | 4/2005 |
| WO | WO2005034810 | 4/2005 |
| WO | WO2005122962 A1 | 12/2005 |
| WO | WO2006007214 | 1/2006 |

* cited by examiner

DEVICE FOR ENABLING REPEATED ACCESS TO A VESSEL

CROSS-REFERENCE TO RELATED APPLICATIONS

This application claims priority of provisional application Ser. No. 61/007,948, filed Dec. 17, 2007.

TECHNICAL FIELD

The present invention relates to a device for enabling repeated access to a blood vessel.

BACKGROUND OF THE INVENTION

There are a number of conditions or procedures which require repeated access to a blood vessel, an important example being hemodialysis.

There are three primary modes of access to the blood in hemodialysis: an intravenous catheter, an arteriovenous (AV) fistula, or a synthetic graft. The type of access is influenced by factors such as the expected time-course of a patient's renal failure and the condition of his or her vasculature. Patients may have multiple accesses, usually because an AV fistula or graft is maturing, and a catheter is still being used.

AV fistulas are recognized as the preferred access method, and are typically situated in the patient's arm (hand, forearm or elbow), but can also be situated in e.g. the patient's leg. To create such a fistula, an artery and a vein are joined together. Since this bypasses the capillaries, blood flows at a high rate through the fistula. This is required since the volumes of blood being withdrawn from, and therefore reintroduced to, the patient are high (typically 150-400 ml/min). Blood from veins is inadequate to meet these flow requirements, and repeated puncture of a large artery is not feasible. Further, a typical vein may not be suitable to handle such high volumes direct from a dialysis machine. Thus, by dividing a vein and connecting it to an artery via an AV fistula, the increased pressure of the blood (due to the blood bypassing the capillary beds) directly entering the vein from the artery enlarges the vein over time and thus allows for higher volumes of blood to be introduced to the vein. A fistula will take a number of weeks to mature, on average perhaps 4-6 weeks.

Access to an AV fistula may commonly be performed via a needle or a cannula, which requires puncturing the wall of the fistula. During a typical treatment, two needles may be inserted into the fistula, one to draw blood and one to return it. Repeated puncturing of the fistula can eventually lead to failure of the fistula via e.g. aneurysm or stenosis, which thereafter may require further surgery to create a new one or to unblock the existing one.

There is a need for a device which aids access to the vasculature, and which can help prevent excessive damage to a blood vessel or fistula occasioned by repeated access.

SUMMARY OF THE INVENTION

Accordingly, in one embodiment of the present invention there is provided an intraluminal device for use in accessing a vessel lumen with a medical implement, said device configured to support the wall of a vessel and comprising at least one device wall defining a device lumen to accommodate flow in said vessel lumen, wherein said device wall comprises at least one fenestration configured to allow access of the medical implement to the device lumen, wherein the at least one fenestration has a reinforced perimeter.

In one aspect of this embodiment, the wall of the device has a reinforced portion opposing the fenestration.

There is also provided a method of facilitating future access to a lumen of a vessel in a body with a medical implement, said method comprising the steps of providing an intraluminal device configured to support the wall of the vessel, said device comprising at least one device wall defining a device lumen to accommodate flow in said vessel lumen, wherein said device wall comprises at least one fenestration configured to allow access of the medical implement to the device lumen; and inserting said device into a body vessel such that the fenestration is accessible percutaneously with said medical implement.

There is also provided a method of accessing a lumen of a vein in a body with a medical implement, said method comprising the steps of creating a fistula between said vein and an artery in said body and implanting an intraluminal device in said lumen of said vein in or proximal to the fistula, wherein said intraluminal device is configured to support the wall of the vein, said device comprising at least one device wall defining a device lumen to accommodate flow in said vein lumen, wherein said device wall comprises at least one fenestration configured to allow access of the medical implement to the device lumen, and wherein access to the lumen of said vein is achievable via said fenestration.

DETAILED DESCRIPTION

Figure 1:
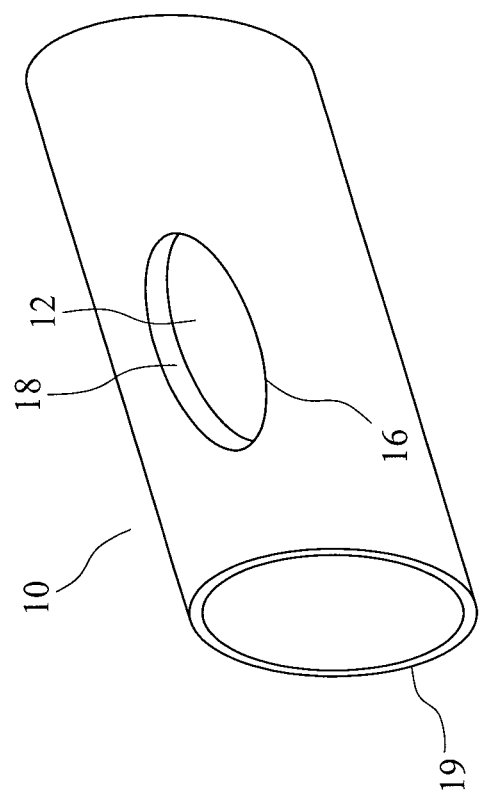
FIG. 1 is a perspective view of an implantable prosthesis according to one embodiment of the present invention.

At least some of the above-mentioned problems may be addressed by an implantable prosthesis according to the present invention and as exemplified in FIGS. 1-6. In particular, and as exemplified in FIG. 1, an implantable prosthesis (10), e.g. in the form of a stent, with at least one fenestration (window) (12) in a side wall (14) is disclosed. The device can be delivered to an AV fistula (or to the vein downstream of the fistula), and is adapted to maintain the integrity of the blood vessel whilst at the same time the window (12) provides an access port through which a medical device (such as a needle or a cannula; not shown) can be directed to enable access to the lumen of the blood vessel which the prosthesis is supporting.

Many different types of stents and stenting procedures are possible. In general, however, stents are typically designed as tubular support structures that may be inserted percutaneously and transluminally through a body passageway. Traditionally, stents are made from a metal or a synthetic material and comprise a network or lattice of structural elements which permits configuration in both a radially-reduced and a radially-expanded geometry. In other words, a series of radial openings extend through the support structure of the stent to facilitate compression and expansion of the stent. One common geometry comprises a plurality of lozenge-shaped or diamond-shaped elements which are joined in a ring and may be expanded from a small diameter configuration to a large diameter configuration. Other common geometries include helically wound wire and filaments, zigzag rings, serpentine rings, and other combinations and derivations of those geometries. It should be noted that FIGS. 1, 2, 3, 4, 5A and 6 are merely schematic representations of exemplified embodiments of the present invention, and as such do not incorporate the detail of the network or lattice of structural elements that may be employed. However, the skilled person will readily understand that in terms of the present invention, a number of geometries, such as those described above, are possible with the present intraluminal device.

Although stents may be made from many types of materials, including non-metallic materials, common examples of metallic materials that may be used to make stents include stainless steel, Nitinol, cobalt-chrome alloys, amorphous metals, tantalum, platinum, gold and titanium. Preferably, the stent is designed in a configuration that allows a large and uniform radial force to be exerted on the vessel wall when the stent is deployed. This is preferred to ensure that the stent, in its expanded state, compresses occlusions and holds the vessel open. A stent that exerts a large and uniform radial force when deployed is also better able to resist external traumas.

Typically, stents are implanted within a passageway by positioning the stent within the area to be treated and then expanding the stent from a compressed diameter to an expanded diameter. The ability of the stent to expand from a compressed diameter makes it possible to thread the stent to the area to be treated through various narrow body passageways while the stent is in the compressed diameter. Once the stent has been positioned and expanded at the area to be treated, the tubular support structure of the stent contacts and radially supports the inner wall of the passageway. As a result, the implanted stent mechanically prevents the passageway from closing and keeps the passageway open to facilitate fluid flow through the passageway.

A wide variety of types of stent can be used in the present invention, adapted to incorporate at least one fenestration, which is configured to allow access by a medical implement, into at least one of its side walls. The stent may comprise drug-coated and/or drug-eluting stents. Drug-coated stents may comprise a therapeutic agent coated alone or in combination with other therapeutic agents/carriers to one or more surfaces (e.g. the struts) of the stent, and which dissolve into the bloodstream. Drug-eluting stents may further comprise hollow elements filled with one or more therapeutic agents. The hollow elements may be wound to define the wall of the stent, and the elements may further comprise holes which allow the therapeutic agent to exit the cavity and enter the bloodstream. The skilled person is aware of the plethora of therapeutic agents that may be used, such as anticoagulants or antibiotics.

In accessing a blood vessel e.g. during hemodialysis, it will be appreciated that a stent may be delivered percutaneously via a stent delivery device to the fistula (or vein) via an entry site in the skin that is close to the final destination of the stent. Alternatively, the intraluminal device may be implanted at the same time as the fistula is created, thus subjecting the patient to fewer surgical steps. Since such delivery methods may not require the delivery device to traverse a tortuous path to the final delivery site (as compared to e.g. a delivery site deep within the body), the skilled person will appreciate that the stent to be used in the present invention does not need to be as radially compressible as stents that may need to be delivered deep in the vasculature. Thus, in one embodiment of the invention, the stent to be used is substantially incompressible or non-expandable.

A typical AV fistula has an inside diameter of about 4-10 mm and a length of about 2-10 cm. The length of the stent typically may depend upon the length of the AV fistula and whether the stent is to extend into one or both of vein and artery. Thus, the length of stent (10) may range from, for example, 1 cm to over 10 cm.

Figure 6:
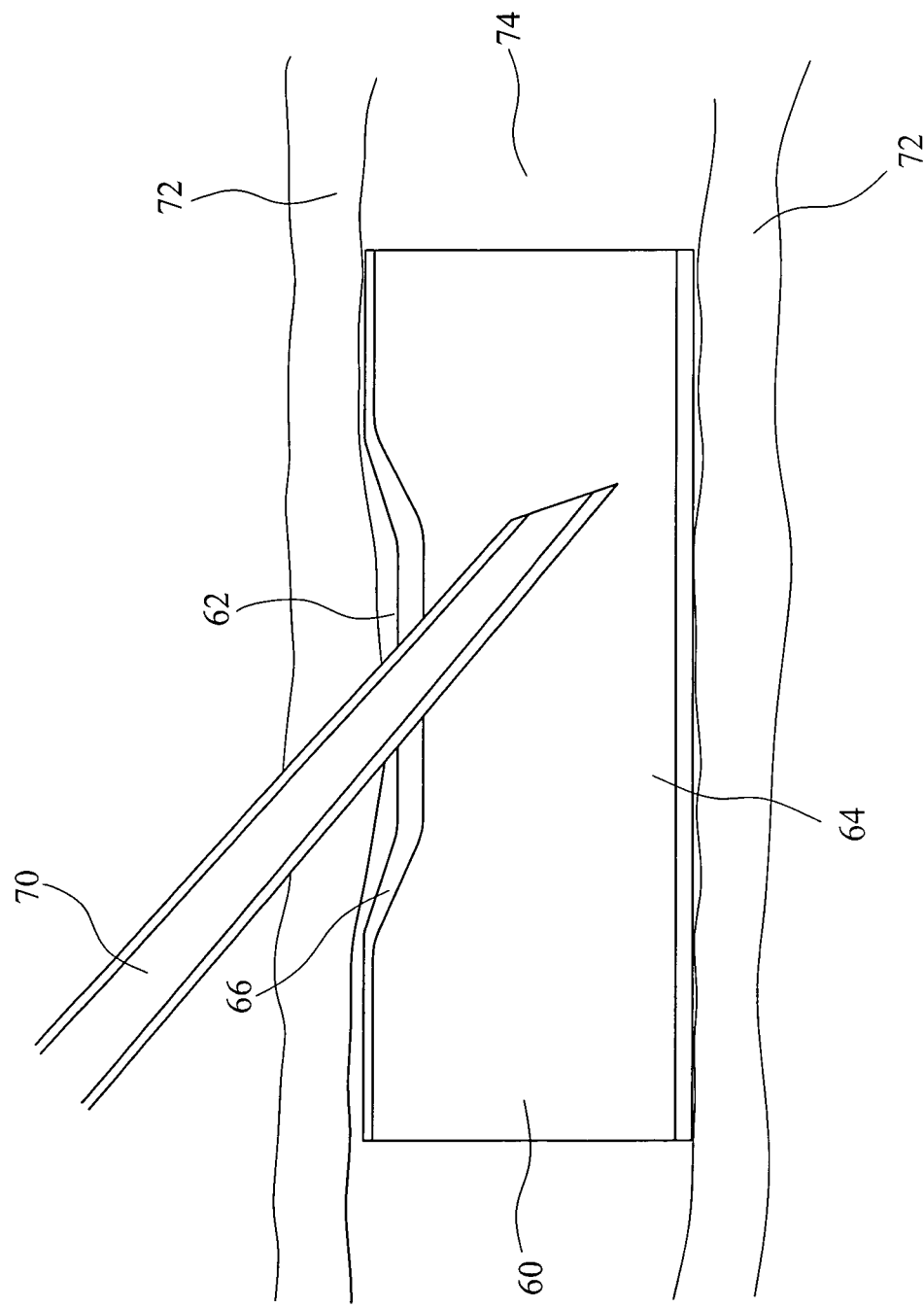
FIG. 6 is a cross-section of one of the embodiments of the prosthesis of the present invention in situ within the vasculature, with a medical device penetrating the vasculature to access the lumen.

As exemplified in FIG. 1, the size of a fenestration (12) may typically vary over a range of about 2 to 10 mm diameter. The shape of the fenestration (12) can be any shape that allows access of a medical device or the like through the fenestration. Examples of shapes of the fenestration include circular, oval, elliptical, hexagonal, octagonal, square, rectangular, etc. Preferably the fenestration is elongate in an axial direction, that is to say the direction in which the device lumen extends, and may be elliptical. Such a configuration may help with the entry of a needle or cannula into the lumen, since such an instrument will typically be inserted into the blood vessel at an oblique angle, as depicted in FIG. 6. It is to be understood that the fenestrations of the present invention are distinct from the numerous radial openings present on a typical stent which result from the configuration of the elements that make up the stent (e.g. a mesh of elements).

As exemplified in FIG. 1, the fenestration (12) that is to be included in the side-wall (14) of the stent (10) is preferably reinforced, by which is meant that the perimeter (16) of the fenestration is reinforced (e.g. more durable than the remainder of the stent). It will be appreciated that the reinforcement of the fenestration perimeter may be achieved in a number of ways. For example, the region of the stent surrounding the fenestration may have a higher density of the struts that form the stent than the density of the struts elsewhere on the stent (see as an example FIG. 5B). However, a more preferable reinforced perimeter may comprise a perimeter of the fenestration that has thicker struts (18) in the perimeter region (16) than are found in the remaining regions of the stent (19). By 'thicker' it is meant wider (axially/circumferentially) and/or deeper (e.g. wall thickness). Such struts are typically integral with the remainder of the stent.

Figure 2:
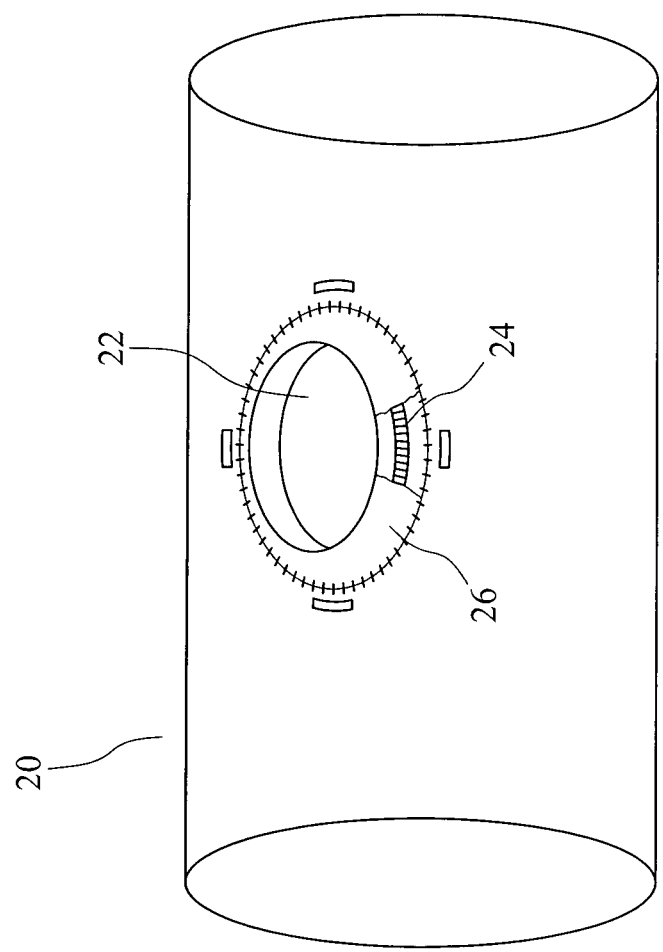
FIG. 2 is a perspective view of an implantable prosthesis according to a further embodiment of the present invention.

An alternative reinforced perimeter is also described herein and exemplified in FIG. 2, which may comprise an expandable reinforcement frame (24) comprising a wire or a stretchable coil loop which is laid on or around the periphery (26) of the fenestration (22). The coil from which the loop is made may be made in an oval shape. The materials used to make the fenestration frame (24) may be any biocompatible material, such as stainless steel, Nitinol, Elgiloy, MP35N, Platinum and many other materials including polymers. Platinum may have the added advantage of providing improved radiopacity of the fenestration, making it easier for the physician to accurately place the fenestration. In addition to the wire and coil loops described, it may also be possible to make stretchable fenestration frames using elastic structures, such as Silicone rubber "O" rings, or any biocompatible elastomer.

If wire is used to make the coil frames of the reinforced perimeter (24), the wire may be in the 0.002 to 0.006 inch (0.05 to 0.15 mm) diameter range. Additionally, flat, square, rectangular and oval wire could also be used to make the coil loop frames. The diameter of the coil in a coil loop frame may be in the 0.01 to 0.05 inch (0.25 to 1.27 mm) range. The long and short axis of an oval-like coil loop frame may be in the 0.005×0.01 inch (0.127 to 0.254 mm) to 0.02×0.05 inch (0.5 to 1.27 mm) range.

The coil loop frame could be made by first coiling the wire to the desired coil diameter by any number of well known coil spring winding techniques and then joining the ends of a length of the coil to form a loop of the desired diameter. The ends of the coil could be welded, soldered or glued together to form the continuous coil loop. The ends of the coil could also be stretched slightly over a distance of e.g. about 1 mm so that the two ends could be threaded or screwed together to form a mechanical connection. The oval coil loop would be made in much the same manner except that the original coil would be pressed or flattened to form the short diameter of the oval.

The above-described reinforcement frame (24) may be attached to the perimeter (26) of the fenestration (22) by any means well known in the art, such as by bonding, welding, soldering or tying points of the frame to the lattice of the stent (20).

Figure 3:
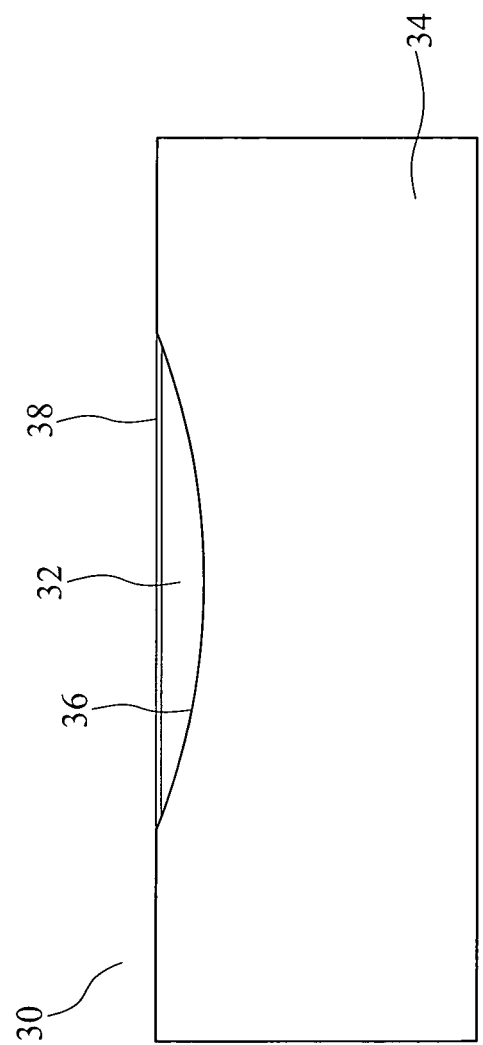
FIG. 3 is a side elevation of an implantable prosthesis according to yet a further embodiment of the present invention.

In a further embodiment of the present invention and as exemplified in FIG. 3, the fenestration (30) may comprise a material which extends at least partially, preferably fully, across the fenestration, thereby providing a cover (38). Such a cover (38) may provide an additional layer of protection to the vessel wall. For example, the cover (38) may help to dissipate the pressure (of the blood) that is directly forced against the vessel wall. This may be beneficial, since on puncturing the vessel wall the integrity of the wall is weakened, which may eventually lead to an aneurysm once the wall is weakened beyond its capacity to resist to outward pressure of the blood. Further, the cover (38) may provide an additional seal against the vessel wall, preventing excessive leakage of blood or its constituents out of the vessel wall into the surrounding tissue. The material of the cover (38) may be any biocompatible material such as any biocompatible polymer such as Dacron and the like and biological materials such as extracellular matrix (ECM) material, for example, small intestine submucosa (SIS) of porcine, bovine and the like. Such a cover (38) may be elastomeric and may preferably self-seal after being punctured.

Optionally, if there is such a cover (38) spanning the fenestration (32), the material of that cover may be integrated with the reinforced perimeter (36) of the fenestration (32), such as by everting the material of the cover around a frame on the perimeter and stitching it back on itself.

Figure 4:
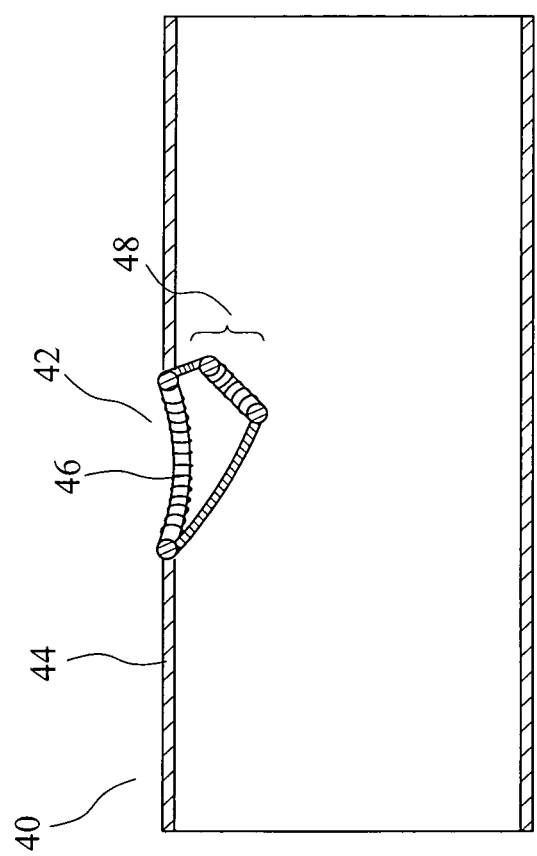
FIG. 4 is a cross-section of an implantable prosthesis according to yet a further embodiment of the present invention.

As depicted in FIG. 4, as an alternative to (or an addition to) the above-mentioned fenestration cover (38), in one embodiment of the stent (40) of the present invention there may be a guiding structure (48) connected to the perimeter (46) of the fenestration (42). This may be a dish-shaped structure, or a conical-like structure, which may enable the medical access device (e.g. a needle or a cannula) to be more easily guided through to the lumen of the stent. Preferably, this guiding structure (48) is integral with the wall (44) of the stent (40), but alternatively it may not be integral and may be attached to the stent (40) by any suitable means, e.g. welding, heat bonding etc. The guiding portion (48) can further act to reinforce the perimeter (46) of the fenestration (42). It may be made from a similar strut-like arrangement as that of the stent (preferably with a higher density of struts), or may be made from portions (lengths) of suitable material, such as metallic or polymeric material.

Figure 5A:
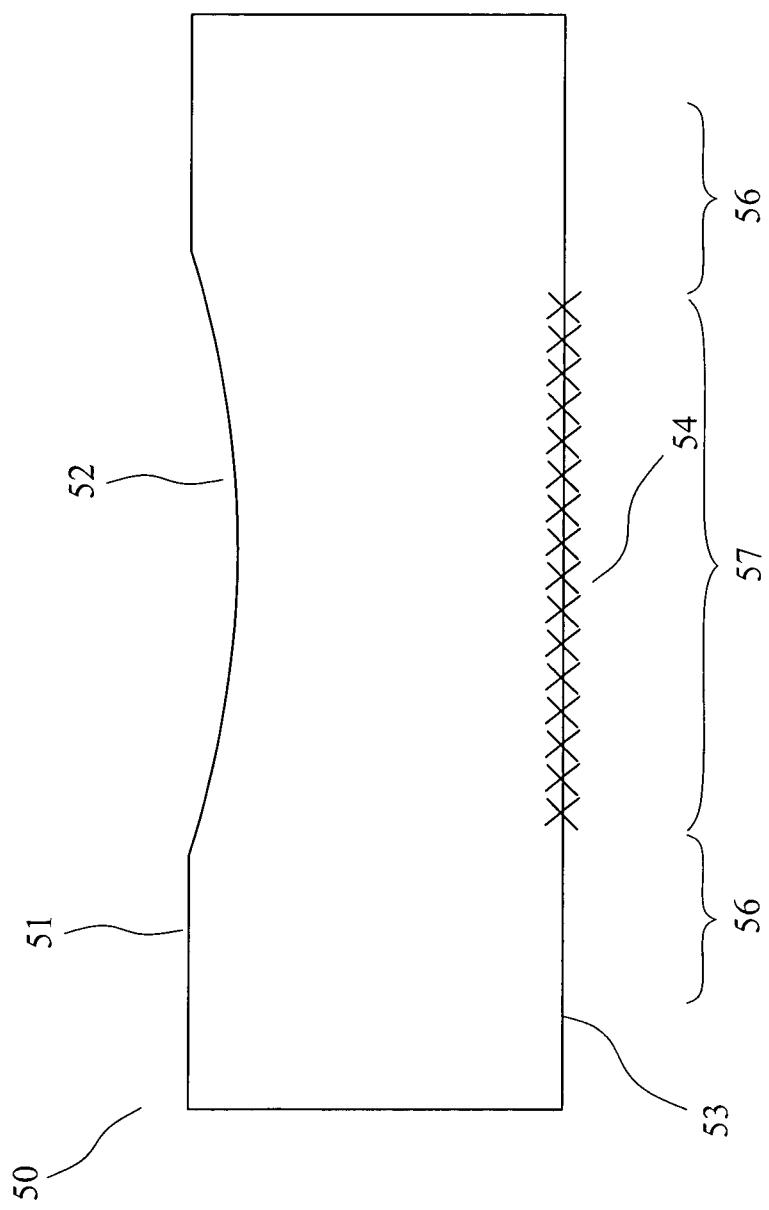
FIG. 5A is a side elevation of an implantable prosthesis according to yet a further embodiment of the present invention.
Figure 5B:
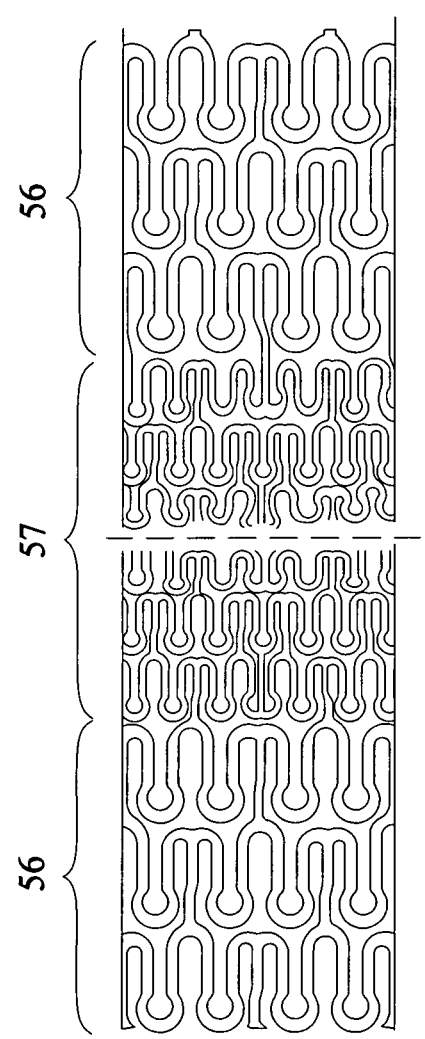
FIG. 5B is an exemplary view of the wall of the prosthesis opposite the fenestration, as depicted in FIG. 5A.

As exemplified in FIGS. 5A and 5B, in a further embodiment of the present invention, in or on the wall (53) opposite the wall (51) where the at least one fenestration (52) is situated there may preferably be a reinforced portion (54) of the stent wall (53). Such a reinforced portion (54) may help to prevent the medical access device (e.g. needle or cannula) from penetrating through to the other side of the vessel (as shown in FIG. 6), since the reinforced portion (54) of the stent (50) will evidently be situated between the lumen of the vessel and the wall of the vessel. As exemplified in FIGS. 5A and 5B, such a reinforced portion (54) of the stent (50) may typically have a higher density of the struts (57) that form the stent than the density of the struts (56) elsewhere on the stent, or a strip of other material (e.g. metal or polymer) may be bonded to, or integral with, the wall of the stent.

In use the stent may be placed into the vein when the AV fistula is initially grafted between the artery and vein, or shortly after. However, it may be the case that the stent might not be used until any time later, possibly until the formation of some blockage in the fistula has been observed. After any necessary removal of the blockage (e.g. via balloon dilation or a cutting balloon), the stent can be mounted to a suitable placement catheter. The placement catheter may be advanced percutaneously into the vein, and then into the venous end of the AV fistula. Proper longitudinal and rotary placement of stent can be monitored using remote visualization techniques, which may or may not involve the use of radiopaque markers carried by the stent. Radiopaque markers, when used, would likely be used at the ends of the stent and/or at the periphery of the fenestration to help ensure proper placement. Alternatively, the material making the frame of the fenestration may be made from a radiopaque material. In addition to using the radiopacity of the fenestration frame to aid in the placement and orientation of the stent, separate radiopaque markers could be added to the stent in the vicinity of or around the periphery of the fenestration. These markers could be gold, platinum, tungsten, etc., bands or wires and could be shaped and/or oriented in such a way so as to indicate rotational orientation fluoroscopically.

Once in position, the stent is released from the placement catheter and is expanded to a working configuration.

The intraluminal device of the present invention is adapted to reside within a blood vessel for a lengthy period of time, since a patient requiring dialysis may receive treatment for a number of years. Thus, the period of time that the device may stay in situ can range from weeks to months, and preferably for a number of years.

As exemplified in FIG. 6, in one example of the invention there is provided a method of accessing a lumen (74) of a body vessel (72), which involves locating an intraluminal device (60) of the present invention which has previously been implanted in said vessel (72), locating said fenestration (62) in said at least one wall (64) of the device (60), and accessing the lumen (74) of the device via said fenestration (62). In order to assist in the location of the fenestration (62), the device may have a profile that is adapted for tactile location of the device percutaneously. In one example, this may be achieved by feeling for the fenestration through the skin (i.e. a change in the resistance of the area over the fenestration may be felt through the skin). However, this may not be ideal if the stent being used has a small fenestration. Thus, in a preferred embodiment, the perimeter of the fenestration has at least one tactile indicium which may be felt through the skin. This may be different from, or the same as, the radiopaque markers that may be present around the fenestration. Alternatively, protrusions or the like may be formed as part of the reinforcing means around the perimeter. These may be integral to, or separate from, the reinforcing means.

Since repeated puncturing of the vessel (72) is inevitable throughout the treatment phase of the patient, in a preferred embodiment of the invention the intraluminal device has more than one window in the same wall, for example two, three, four or more windows. This allows for alternating access areas to the vessel, so that the wall of the vessel is given time to heal before it is re-punctured at the same point at a later date. Once the stent (60) has been positioned in the vessel (72) it preferably will not rotate or otherwise move within the vessel. Thus, it will be appreciated that the fenestration must be positioned such that access can be achieved from outside of the skin. Thus, when the stent comprises two or more fenestrations, it will be appreciated that those fenestrations should be on the same wall and axially spaced from each other, such that each is accessible from outside of the skin.

Preferably, two stents may be delivered along the fistula or vein, wherein one may be used for withdrawing blood from the vasculature, and one may be used to introduce blood back to the vasculature once it has been passed through a dialysis machine. Alternatively, one stent with multiple windows may be delivered to the fistula or vein, and access for withdrawing and reintroducing the blood from and to the body can be performed via different fenestrations in the single stent. Such a stent may be optionally longer than stents with fewer windows.

Thus, in one embodiment, the stent facilitates future access to a lumen of a vessel in a body, since after inserting said device into a body vessel the fenestration may be easily accessible percutaneously by a hypodermic needle (70) or cannula (70).

Of course, the skilled person will realise that the stent of the present invention may likewise be used anywhere within the vasculature, where it may function to e.g. provide support to bifurcated vessels. In such a case, the reinforced fenestration may be particularly desirable if another like stent, or any other type of stent, were to be configured with the stent of the present invention to form a branched stent, in the form of e.g. a 'T'-shaped or a 'Y'-shaped junction. Further, although the present invention has been illustrated mainly with references to hemodialysis, it is to be understood that the stent of the present invention may be used in any situation where repeated access to the vasculature is required.

What is claimed is:

1. An intraluminal device for use in accessing a vessel lumen with a medical implement, the intraluminal device comprising:
    a lattice of structural elements forming a tubular shape having a device wall defining a device lumen, the device wall having a fenestration side and an opposite side located opposite the fenestration side;
    a fenestration disposed in the fenestration side of the device wall, the fenestration passing through the fenestration side of the device wall allowing access of the medical implement to the device lumen through the fenestration side of the device wall;
    a reinforced perimeter on the fenestration side around the fenestration; and
    a reinforced portion opposing the fenestration, the reinforced portion formed in the opposing side of the device wall.

2. The device of claim 1, wherein the reinforced perimeter is reinforced along substantially the whole of the perimeter of the fenestration.

3. The device of claim 1, wherein the reinforced perimeter comprises a greater thickness of the material of the device than that which makes up the rest of the device.

4. The device of claim 1, wherein the reinforced perimeter comprises a frame disposed about the fenestration.

5. The device of claim 4, wherein the frame is expandable.

6. The device of claim 1, wherein the reinforced perimeter further comprises at least one marker suitable for locating the fenestration.

7. The device of claim 6, wherein the at least one marker is radiopaque.

8. The device of claim 1, wherein the device further comprises a cover that extends at least partially across the fenestration.

9. The device of claim 8 wherein the cover is elastomeric.

10. An intraluminal device for use in accessing a vessel lumen with a medical implement, the intraluminal device comprising:
    a device wall defining a device lumen, wherein the device wall comprises a fenestration side and an opposite side located opposite the fenestration side;
    a fenestration disposed in the fenestration side, the fenestration passing through the device wall allowing access of the medical implement to the device lumen through the device wall;
    a reinforced perimeter of the device wall around the fenestration;
    a guiding structure disposed in the device wall about the fenestration, the guiding structure forming a conical entrance into the fenestration; and
    a reinforced portion opposing the fenestration, the reinforced portion formed in the opposing side of the device wall.

11. The device of claim 1, wherein the fenestration is elongate in a direction in which the device lumen extends.

12. An intraluminal device for use in accessing a vessel lumen with a medical implement, the intraluminal device comprising:
    a device wall having a fenestration side and an opposite side opposite the fenestration side, the device wall defining a device lumen;
    a fenestration disposed in the fenestration side of the device wall, the fenestration providing access to the device lumen through the device wall;
    a reinforced perimeter formed in the device wall around the fenestration; and,
    a reinforced portion opposing the fenestration, the reinforced portion formed in the opposing side of the device wall.

13. The intraluminal device of claim 12, wherein the reinforced portion comprises a higher density of struts in the reinforced portion than outside of the reinforced portion.

14. The intraluminal device of claim 1, wherein the intraluminal device has two fenestrations spaced in the direction in which the device lumen extends.

15. The intraluminal device of claim 1, wherein the intraluminal device carries a drug for release in the vessel.

16. An intraluminal device for implantation into the lumen of an arteriovenous fistula and for use in accessing the lumen of the arteriovenous fistula with a medical implement, the intraluminal device comprising a device wall defining a device lumen, the device wall having a fenestration side and an opposite side;

a fenestration formed in the fenestration side of the device wall providing access to the device lumen through the device wall;

a reinforced perimeter formed in the device wall around the fenestration; and a reinforced portion opposing the fenestration, the reinforced portion formed in the opposing side of the device wall.

17. The intraluminal device of claim 16, wherein the device wall comprises a lattice of structural elements.

18. The intraluminal device of claim 16, wherein the intraluminal device is substantially tubular in shape.

19. The intraluminal device of claim 1, wherein the reinforced portion comprises a higher density of struts in the reinforced portion than outside of the reinforced portion.

20. The intraluminal device of claim 16, wherein the reinforced perimeter is reinforced along substantially the whole of the perimeter of the fenestration, the reinforced perimeter comprises a greater thickness of the material of the device than that which makes up the rest of the device, the device further comprises a cover that extends at least partially across the at least one fenestration, and the cover is elastomeric.

21. The intraluminal device of claim 20, wherein the reinforced portion comprises a higher density of struts in the reinforced portion than outside of the reinforced portion.

22. The intraluminal device of claim 21, wherein the reinforced perimeter comprises a frame disposed about the fenestration, and the frame is expandable.

* * * * *